United States Patent [19]
Tracy et al.

[11] Patent Number: 5,711,968
[45] Date of Patent: Jan. 27, 1998

[54] COMPOSITION AND METHOD FOR THE CONTROLLED RELEASE OF METAL CATION-STABILIZED INTERFERON

[75] Inventors: Mark A. Tracy, Arlington; Howard Bernstein, Cambridge, both of Mass.; M. Amin Khan, Dowingtown, Pa.

[73] Assignee: Alkermes Controlled Therapeutics, Inc., Cambridge, Mass.

[21] Appl. No.: 279,784

[22] Filed: Jul. 25, 1994

[51] Int. Cl.⁶ ............................. A61K 9/10; A61K 9/16
[52] U.S. Cl. .................. 424/487; 424/486; 424/488; 424/499; 424/501; 424/443; 424/444; 424/423; 424/426; 424/434; 424/436
[58] Field of Search .......................... 424/486, 487, 424/488, 499, 501, 422, 423, 426, 443–444, 85.4–85.7; 514/2; 530/351, 814, 815

[56] References Cited

U.S. PATENT DOCUMENTS

| | | | |
|---|---|---|---|
| 3,928,566 | 12/1975 | Briggs et al. | 424/94 |
| 4,166,800 | 9/1979 | Fong | 252/316 |
| 4,252,791 | 2/1981 | Grossberg et al. | 424/85 |
| 4,530,901 | 7/1985 | Weissmann | 435/70 |
| 4,675,189 | 6/1987 | Kent et al. | 424/490 |
| 4,853,218 | 8/1989 | Yim et al. | 424/85.7 |
| 4,871,538 | 10/1989 | Yim et al. | 424/85.7 |
| 4,897,268 | 1/1990 | Tice et al. | 424/422 |
| 4,962,091 | 10/1990 | Eppstein et al. | 514/2 |
| 5,019,400 | 5/1991 | Gombotz et al. | 424/497 |
| 5,126,147 | 6/1992 | Silvestri et al. | 424/497 |
| 5,192,741 | 3/1993 | Orsolini et al. | 514/4 |
| 5,441,734 | 8/1995 | Reichert et al. | 424/85.7 |

FOREIGN PATENT DOCUMENTS

| | | |
|---|---|---|
| 0 123 291 A2 | 10/1984 | European Pat. Off. |
| 0 281 299 A1 | 9/1988 | European Pat. Off. |
| 0 307 097 A2 | 3/1989 | European Pat. Off. |
| 0 633 020 A1 | 1/1995 | European Pat. Off. |
| WO 91/12882 | 9/1991 | WIPO |
| WO 91/18927 A1 | 12/1991 | WIPO |
| WO 92/11844 | 7/1992 | WIPO |
| WO 93/25221 | 12/1993 | WIPO |
| WO 93/17668 | 3/1994 | WIPO |
| WO 94/12158 | 6/1994 | WIPO |
| WO 94/19373 A1 | 9/1994 | WIPO |

OTHER PUBLICATIONS

S. Nagata, et al., "Synthesis in *E. coli* of Polypetide with Human Leukocyte Interferon Activity," *Nature*, 284:316–320 (Mar. 1980).

M. Rubinstein, "The Structure of Human Interferons," *Biochimica et Biophysica Acta.*, 695:5–16 (1982).

B. C. Cunningham, et al., "Dimerization of Human Growth Hormone by Zinc," *Science*, 253:545–548 (2 Aug. 1991).

Chemistry, Macifil et al, D. C. Heath & Co, 1978, pp. 156–157.

*Primary Examiner*—Edward J. Webman
*Attorney, Agent, or Firm*—Hamilton, Brook, Smith & Reynolds, P.C.

[57] ABSTRACT

This invention relates to a composition, and method of forming said composition, for the controlled release of interferon. The controlled release composition of this invention comprises a biocompatible polymer and particles of metal cation-stabilized interferon, wherein the particles are dispersed within the biocompatible polymer.

The method of the invention, for producing a composition for the controlled release of interferon, includes dissolving a polymer in a polymer solvent to form a polymer solution, dispersing particles of metal cation stabilized-interferon particles in the polymer solution, and then solidifying the polymer to form a polymeric matrix containing a dispersion of the interferon particles.

29 Claims, 5 Drawing Sheets

COMPOSITION AND METHOD FOR THE CONTROLLED RELEASE OF METAL CATION-STABILIZED INTERFERON

BACKGROUND OF THE INVENTION

Interferon acts to mediate natural immunity to protect against viral infection and to initiate inflammatory reactions that protect against bacterial infections. Interferon has also been shown to be an effective anti-tumor or anticancer agent.

Previously, the administration of interferon has often required frequent subcutaneous injections, given at intervals which resulted in fluctuating medication levels. However, many conditions treated by interferon therapy may respond better to controlled levels of interferon which may provide more effective prophylactic or therapeutic effects.

Attempts to control and sustain medication levels in humans or animals between the administration of doses have more recently included the use of biodegradable polymers as matrices for controlling the release of medicaments. In some cases, biodegradable polymers, under in vivo conditions, exhibited high initial bursts of medicament release and minimal release thereafter Furthermore, methods used to form controlled release compositions have often resulted in a loss of activity of the medicament due to the instability of the medicament, chemical interactions between the medicament and the other components contained in, or used in formulating, the controlled release composition, or have resulted in losses of medicament due to the formulation process.

Therefore, a need exists for a means of controlling the release of interferon while not reducing the activity, or potency, of the interferon released.

SUMMARY OF THE INVENTION

This invention relates to a composition, and method of forming said composition, for the controlled release of interferon. The controlled release composition of this invention comprises a biocompatible polymer and particles of metal cation-stabilized interferon, wherein the particles are dispersed within the biocompatible polymer.

The method of the invention, for producing a composition for the controlled release of interferon, includes dissolving a polymer in a polymer solvent to form a polymer solution, dispersing particles of metal cation-stabilized interferon in the polymer solution, and then solidifying the polymer to form a polymeric matrix containing a dispersion of the metal cation-stabilized interferon particles.

The advantages of a controlled release formulation for interferon include increased patient compliance and acceptance by reducing the number of subcutaneous injections, increased therapeutic benefit by eliminating fluctuations in interferon concentration in blood levels, and potentially lowering the total administered amount of interferon by reducing these fluctuations. The advantages further include a reduction of the loss of the interferon's biological activity which allows for the use of a lower amount of interferon to form a controlled release composition.

DETAILED DESCRIPTION OF THE INVENTION

Figure 1:
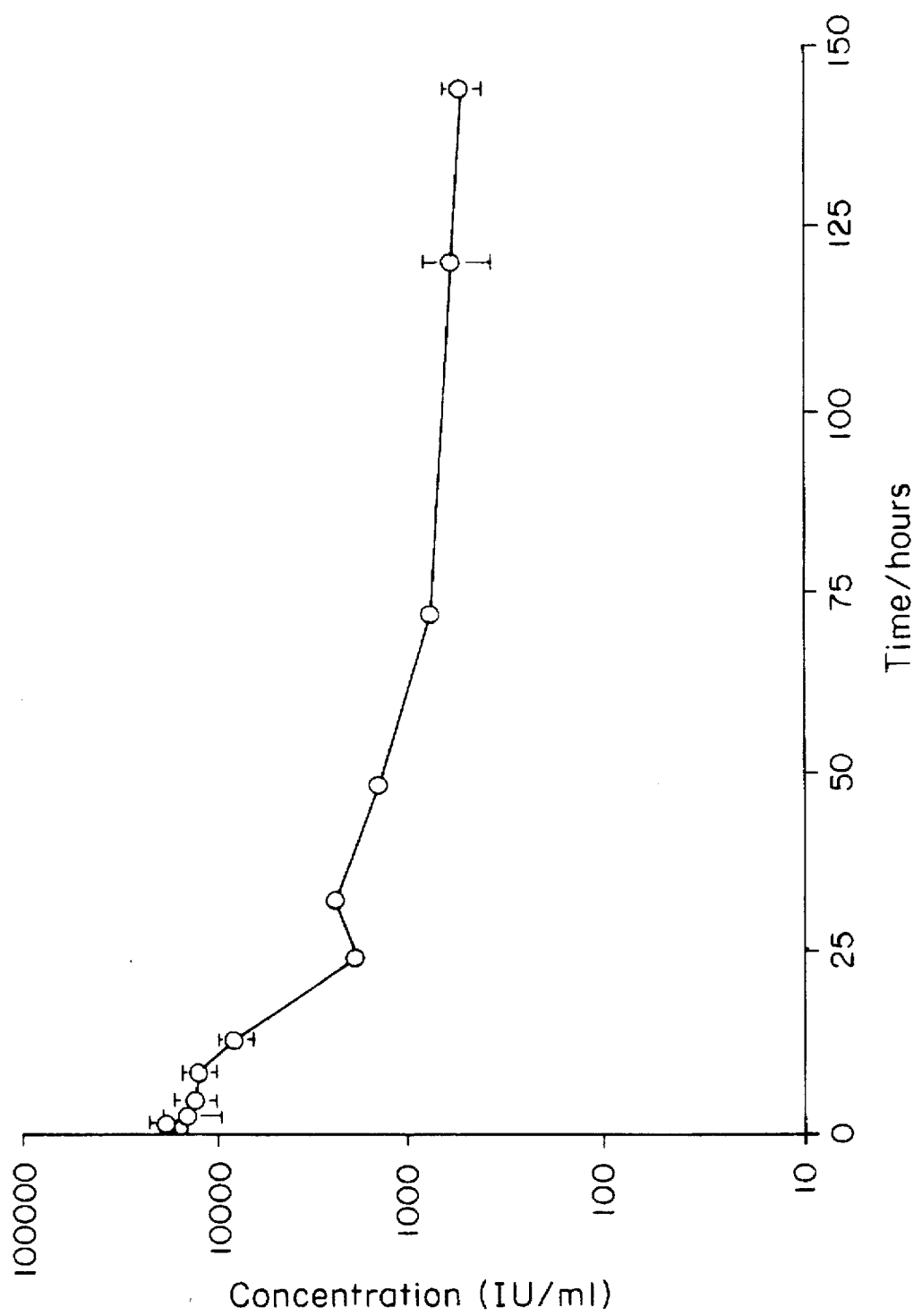
FIG. 1 is a plot of the serum concentration (IU/mL) of Interferon-α,2b in rats which were subcutaneously administered Interferon-α,2b controlled release microspheres of Example 2, versus time over a 6 day interval. The error bars provide the standard deviation in the values of Interferon-α,2b concentrations for the four rats tested.

Interferon (IFN), as defined herein, includes all forms of IFN, such as IFN-α, IFN-β and IFN-γ. IFN can be derived from animal sources or can be cloned and purified as described in Rubenstein et al., *Biochem. Biophys. Acta*, 695: 705–716 (1982), Nagata et al., *Nature*, 284: 316–320 (1980), U.S. Pat. No. 4,289,690, issued to Pestka et al. and U.S. Pat. No. 4,530,901, issued to C. Weissmann.18

As defined herein, a controlled release of interferon is a sustained and/or modulated release of IFN from a biocompatible polymeric matrix. In a sustained release, IFN release occurs over a period which is longer than that period during which a biologically significant amount of IFN would be released following direct administration of a solution of IFN. It is preferred that a sustained release be a release of IFN over a period of up to about three to about six months. A sustained release of IFN from a polymeric matrix can be continuous or non-continuous release with relatively constant or varying rates of release. The continuity of IFN release and level of IFN release can be established by using one or more types of polymer compositions, IFN loadings, and/or selection of excipients to produce the desired effect.

In a modulated IFN release, which results when a suitable metal cation component is dispersed within the polymeric matrix, at least one IFN release characteristic, such as the IFN initial release level, the subsequent IFN release levels, duration of release and/or the amount of IFN released, is different from the release characteristics exhibited by IFN being released from a polymeric matrix, wherein the polymeric matrix does not contain a dispersed metal cation component.

Metal cation-stabilized interferon (hereinafter "$M^{+n}$-stabilized IFN"), as defined herein, comprises a lyophilized particle containing biologically active IFN and at least one type of multivalent metal cation, having a valency of +2 or more, wherein the cation is not significantly oxidizing to IFN. Thus for $M^{+n}$, n is an integer equal to 2 or more. It is preferred that the $M^{+n}$ be complexed with the IFN. In $M^{+n}$-stabilized IFN, the tendency of IFN to aggregate within a microparticle during hydration and/or to lose biological activity or potency due to the process of forming a controlled release composition or due to the chemical characteristics of a controlled release composition, is reduced by mixing metal cations ($M^{+n}$) with the IFN prior to lyophilizing to form $M^{+n}$-stabilized IFN particles. The $M^{+n}$-stabilized IFN particles are subsequently dispersed within a polymeric matrix to form a controlled release composition of this invention.

Suitable IFN-stabilizing metal cations include biocompatible multivalent metal cations which will not significantly oxidize IFN. Typically, oxidation of IFN by a metal cation is not significant if this oxidation results in a loss of IFN potency of about 10% or less. A metal cation is biocompatible if the cation is non-toxic to the recipient, in the quantities used, and also presents no significant deleterious or untoward effects on the recipient's body, such as an immunological reaction at the injection site.

Examples of suitable, IFN-stabilizing metal cations include cations of nontransition metals, such as $Mg^{+2}$ and $Ca^{+2}$. Suitable IFN-stabilizing metal cations also include cations of transition metals, such as $Cu^{+2}$. In a preferred embodiment, $Zn^{+2}$ is used as a IFN-stabilizing metal cation. The suitability of metal cations for stabilizing IFN can be determined by one of ordinary skill in the art by performing a variety of stability indicating techniques such as polyacrylamide gel electrophoresis, isoelectric focusing, reverse phase chromatography, HPLC and potency tests on IFN lyophilized particles containing metal cations to determine the potency of the IFN after lyophilization and for the duration of release from microparticles, as described in Example 7.

Polymers suitable to form a polymeric matrix of the controlled release composition of this invention are biocompatible polymers which can be either biodegradable or non-biodegradable. Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons.

A polymer is biocompatible if the polymer, and any degradation products of the polymer, are non-toxic to the recipient and also present no significant deleterious or untoward effects on the recipient's body, such as an immunological reaction at the injection site. Suitable biocompatible, non-biodegradable polymers include, for instance, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Suitable biocompatible, biodegradable polymers include, for example, poly(lactides), poly(glycolides), poly(lactide-co-glycolides), polycaprolactone, polycarbonates, polyesteramides, polyanhydrides, poly(amino acids), polyorthoesters, polyacetals, polycyanoacrylates, degradable polyurethanes, blends and copolymers thereof. Polymers comprising poly(lactides), copolymers of lactides and glycolides, blends thereof, or mixtures thereof are preferred. Said polymers can be formed from monomers of a single isomeric type or a mixture of isomers.

The amount of IFN, which is contained in the $M^{+n}$-stabilized IFN particles dispersed within the polymeric matrix of a controlled release composition is a therapeutically, prophylactically or diagnostically effective amount, which can be determined by a person of ordinary skill in the art taking into consideration factors such as body weight, condition to be treated, type of polymer used, and release rate from the polymer.

In one embodiment, an IFN controlled release composition will contain from about less than 0.01% (w/w) to approximately 50% (w/w) IFN. The amount of IFN used will vary depending upon the desired effect of the IFN, the planned release levels, and the time span over which the IFN will be released. A preferred range of IFN loading is between about 0.1% (w/w) to about 30% (w/w) IFN. A more preferred range of IFN loading is between about 0.5% (w/w) to about 15% (w/w) IFN.

In another embodiment, an IFN controlled release composition also contains a second metal cation component, which is not contained in the $M^{+n}$-stabilized IFN particles, and which is dispersed within the polymer. The second metal cation component can optionally contain the same species of metal cation, as is contained in the $M^{+n}$-stabilized IFN, and/or can contain one or more different species of metal cation. The second metal cation component acts to modulate the release of the IFN from the polymeric matrix of the controlled release composition and can enhance the stability of IFN in the composition. A metal cation component used in modulating release typically comprises at least one type of multivalent metal cations. Examples of second metal cation components suitable to modulate IFN release, include, or contain, for instance, $Mg(OH)_2$, $MgCO_3$ (such as $4MgCO_3 \cdot Mg(OH)_2 \cdot 5H_2O$), $ZnCO_3$ (such as $3Zn(OH)_2 \cdot 2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3(C_6H_5O_7)_2$. A suitable ratio of second metal cation component-to-polymer is between about 1:99 to about 1:2 by weight. The optimum ratio depends upon the polymer and the second metal cation component utilized. A polymeric matrix containing a dispersed metal cation component to modulate the release of a biologically active agent from the polymeric matrix is further described in co-pending U.S. patent application Ser. No. 08/237,057, the teachings of which are incorporated herein by reference.

In yet another embodiment, at least one pore forming agent, such as a water soluble salt, sugar or amino acid, is included in the microparticle to modify the microstructure of the microparticle. The proportion of pore forming agent added to the polymer solution is between about 1% (w/w) to about 30% (w/w). It is preferred that at least one pore forming agent be included in a nonbiodegradable polymeric matrix of the present invention.

The interferon in an IFN controlled release composition can also be mixed with other excipients, such as stabilizers, solubility agents and bulking agents. Stabilizers are added to maintain the potency of the IFN over the duration of IFN release. Suitable stabilizers include, for example, carbohydrates, amino acids, fatty acids and surfactants and are known to those skilled in the art. The amount of stabilizer used is based on ratio to the IFN on a weight basis. For amino acids, fatty acids and carbohydrates, such as sucrose, lactose, mannitol, dextran and heparin, the molar ratio of carbohydrate to IFN is typically between about 1:10 and about 20:1. For surfactants, such as Tween™ and Pluronic™, the molar ratio of surfactant to IFN is typically between about 1:1000 and about 1:20.

Solubility agents are added to modify the solubility of IFN. Suitable solubility agents include complexing agents, such as albumin and protamine, which can be used to control the release rate of IFN from a polymeric matrix. The weight ratio of solubility agent to IFN is generally between about 1:99 and about 20:1.

Bulking agents typically comprise inert materials. Suitable bulking agents are known to those skilled in the art.

The IFN controlled release composition of this invention can be formed into many shapes such as a film, a pellet, a cylinder, a disc or a microparticle. A microparticle, as defined herein, comprises a polymeric component having a diameter of less than about one millimeter and having $M^{+n}$-stabilized IFN particles dispersed therein. A microparticle can have a spherical, non-spherical or irregular shape. It is preferred that a microparticle be a microsphere. Typically, the microparticle will be of a size suitable for injection. A preferred size range for microparticles is from about 1 to about 180 microns in diameter.

In the method of this invention for forming an IFN controlled release composition, a suitable amount of $M^{+n}$-stabilized IFN particles are dispersed within a polymer solution. The IFN particles can be dispersed with the polymer solution by stirring, agitation, sonication or by other known mixing means. The polymer solution, having a dispersion of $M^{+n}$-stabilized IFN particles is then solidified, by appropriate means, to form an IFN controlled release composition of this invention.

Alternately, particles of $M^{+n}$-stabilized IFN and a polymer can be mixed into a polymer solvent sequentially, in reverse order, intermittently, separately or through concurrent additions, to form a dispersion of $M^{+n}$-stabilized IFN particles in a polymer solution.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 5% (w/w) to about 20% (w/w) polymer. A polymer solution containing 10% to about 15% (w/w) polymer is most preferred.

A suitable polymer solvent, as defined herein, is solvent in which the polymer is soluble but in which the $M^{+n}$-IFN particles are substantially insoluble and nonreactive. Examples of suitable polymer solvents include polar organic liquids, such as methylene chloride, chloroform and acetone.

To prepare $M^{+n}$-stabilized IFN particles, interferon is mixed in a suitable solvent with at least one suitable IFN-stabilizing metal cation to form a $M^{+n}$-IFN mixture, wherein each component of the mixture can be in suspension or solution, or a combination thereof. In forming $M^{+n}$-stabilized IFN, the molar ratio of $M^{+n}$:IFN in solution is typically between about 1:2 and about 100:1, and is preferentially between about 1:1 and about 10:1. The concentration of IFN in solution is typically between about 0.1 to about 20 mg IFN/mL of solvent, and preferentially, between about 1.0 to about 5.0 mg IFN/mL of solvent.

It is understood that the IFN can be in a solid or a dissolved state, prior to being contacted with the metal cation component. It is also understood that the metal cation component can be in a solid or a dissolved state, prior to being contacted with the IFN. In a preferred embodiment, a buffered aqueous solution of IFN is mixed with an aqueous solution of the metal cation component.

Suitable solvents are those in which the IFN and the metal cation component are each at least slightly soluble, such as in an aqueous sodium bicarbonate buffer or in an aqueous phosphate buffer. For aqueous solvents, it is preferred that water used be either deionized water or water-for-injection (WFI).

The $M^{+n}$-IFN mixture is then dried, such as by lyophilization, to form particulate $M^{+n}$-stabilized IFN. The $M^{+n}$-IFN mixture can be bulk lyophilized or can be divided into smaller volumes which are then lyophilized. In a preferred embodiment, the $M^{+n}$-IFN mixture is micronized, such as by use of an ultrasonic nozzle, and then lyophilized to form $M^{+n}$-stabilized IFN particles. Acceptable means to lyophilize the $M^{+n}$-IFN mixture include those known in the art.

In a preferred embodiment, interferon is contacted with at least one suitable IFN-stabilizing metal cation, such as $Ca^{+2}$, and with a suitable solvent, under pH conditions suitable for forming a complex of $M^{+n}$ and IFN. Typically, the $M^{+n}$-complexed IFN will be in the form of a cloudy precipitate, which is suspended in the solvent. However, the $M^{+n}$-complexed IFN can also be in solution. In an even more preferred embodiment, IFN is complexed with $Zn^{+2}$.

Suitable pH conditions to form a complex of $M^{+n}$ and IFN typically include pH values between about 4.0 and about 8.0. A preferred pH range is between about 5.0 and about 7.4. Suitable pH conditions are typically achieved through use of an aqueous buffer, such as sodium bicarbonate, as the solvent. The synthesis of $Zn^{+2}$-stabilized IFN particles is further described in Example 1.

In one embodiment of the method of this invention, a suitable amount of $M^{+n}$-stabilized IFN particles is added to a polymer solution. In another embodiment, a second metal cation component, which is not contained in $M^{+n}$-stabilized IFN particles, is also dispersed within the polymer solution.

It is understood that a second metal cation component and $M^{+n}$-stabilized IFN can be dispersed into a polymer solution sequentially, in reverse order, intermittently, separately or through concurrent additions. Alternately, a polymer, a second metal cation component and $M^{+n}$-stabilized IFN and can be mixed into a polymer solvent sequentially, in reverse order, intermittently, separately or through concurrent additions. The method for forming a composition for modulating the release of a biologically active agent from a biodegradable polymer is further described in co-pending U.S. patent application Ser. No. 08/237,057.

One suitable method for forming an IFN controlled release composition from a polymer solution is the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al. Solvent evaporation is typically used as a method to form IFN controlled release microparticles.

In the solvent evaporation method, a polymer solution containing an $M^{+n}$-stabilized IFN particle dispersion, is mixed in or agitated with a continuous phase, in which the polymer solvent is partially miscibile, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of $M^{+n}$-stabilized IFN particles contained therein.

A preferred method for forming IFN controlled release microparticles from a polymer solution is described in U.S. Pat. No. 5,019,400, issued to Gombotz et al. The teachings of U.S. Pat. No. 5,019,400 are incorporated herein by reference. This method of microsphere formation, as compared to other methods, such as phase separation, additionally reduces the amount of interferon required to produce a controlled release composition with a specific interferon content. Also see Examples 2–6 for additional descriptions of microparticle formulations.

In this method, the polymer solution, containing the $M^{+n}$-stabilized IFN particle dispersion, is processed to create droplets, wherein at least a significant portion of the droplets contain polymer solution and $M^{+n}$-stabilized IFN particles. These droplets are then frozen by means suitable to form microparticles. Examples of means for processing the polymer solution dispersion to form droplets include directing the dispersion through an ultrasonic nozzle, pressure nozzle, Rayleigh jet, or by other known means for creating droplets from a solution.

Means suitable for freezing droplets to form microparticles include directing the droplets into a liquified gas, such as liquid argon and liquid nitrogen. The microparticles then sink to the surface of a frozen non-solvent, such as ethanol, or ethanol mixed with hexane or pentane. The liquid gas is subsequently evaporated and the microparticles then sink into the non-solvent as the non-solvent thaws.

Alternately, the droplets can be frozen to form microparticles by directing the droplets into a supercooled liquid. A supercooled liquid is suitable when the liquid is a non-solvent for the polymer and is at a temperature significantly below the freezing point of the droplet.

The solvent in the microparticles is extracted into the non-solvent to form $M^{+n}$-stabilized IFN containing microparticles. Mixing ethanol with other non-solvents, such as hexane or pentane, can increase the rate of solvent extraction, above that achieved by ethanol alone, from certain polymers, such as poly(lactide-co-glycolide) polymers. It is important that the polymer/active agent freeze upon contacting the cold liquid, and then be slowly thawed and the polymer solvent extracted from the microparticles.

The thawing rate is dependent on the choice of solvent and non-solvent. A suitable solvent typically has a higher melting point than the non-solvent so that the non-solvent melts first, allowing the frozen microparticles to sink into the liquid wherein the polymer solvent subsequently melts. As the solvent in the microparticles melts, it is extracted into the non-solvent. The solvent for the polymer and the non-solvent for the polymer must be miscible to allow extraction of the solvent from the microparticles.

A wide range of sizes of IFN controlled release microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. The size of the microparticles produced by this process can range from greater than 1000 to 1 microns in diameter.

Yet another method of forming an IFN controlled release composition, from a polymer solution, includes film casting, such as in a mold, to form a film or a shape. For instance, after putting the polymer solution containing a dispersion of $M^{+n}$-stabilized IFN particles into a mold, the polymer solvent is then removed by means known in the art, or the temperature of the polymer solution is reduced, until a film or shape, with a consistent dry weight, is obtained. Film casting of a polymer solution, containing a biologically active agent, is further described in co-pending U.S. patent application Ser. No. 08/237,057.

The method of this invention for forming an IFN controlled release composition can also be used to form a controlled release composition of another cytokine, wherein the cytokine is similarly susceptible to agglomeration during hydration and/or to a loss of activity, or potency, due to the process of formation or the chemical characteristics of the controlled release composition.

It is believed that the release of the IFN can occur by two different mechanisms. The IFN can be released by diffusion through aqueous filled channels generated in the polymeric matrix, such as by the dissolution of the IFN or by voids created by the removal of the polymer's solvent during the synthesis of the controlled release composition. A second mechanism is the release of IFN due to degradation of the polymer.

Polymer degradation can occur by hydrolysis of the ester linkages on the backbone. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of the polymer, the contributions of diffusion and/or polymer degradation to IFN release can be controlled. For example, increasing the glycolide content of a poly(lactide-co-glycolide) polymer and decreasing the molecular weight of the polymer can enhance the hydrolysis of the polymer and thus, provides an increased IFN release from polymer erosion.

In addition, the rate of polymer hydrolysis is increased in non-neutral pH's. Therefore, an acidic or a basic excipient can be added to the polymer solution, used to form the microsphere, to alter the polymer erosion rate.

The composition of this invention can be administered to a human, or other animal, by injection or implantation subcutaneously, intramuscularly, intraperitoneally, and intradermally, by administration to mucosal membranes, such as intranasally or by means of a suppository, or by in situ delivery (e.g. by enema or aerosol spray) to provide the desired dosage of IFN based on the known parameters for treatment with IFN of the various medical conditions.

The invention will now be further and specifically described by the following examples.

EXAMPLE 1

Formation of $Zn^{+2}$-Stabilized Interferon

IFN-α,2b, which was used in the present Examples, is identical to IFN-α,2 as described in Rubenstein et al., *Biochem. Biophys. Acta*, 695: 705–716 (1982), with the exception that the lysine at position 23 of IFN-α,2 is an arginine in IFN-α,2b. The IFN-α,2b was dissolved in different volumes of 10 mM sodium bicarbonate buffer (pH 7.2) to form IFN solutions with concentrations between 0.1 and 0.5 mM IFN. A 10 mM $Zn^{+2}$ solution was prepared from deionized water and zinc acetate dihydrate and then was added to the IFN solutions to form $Zn^{+2}$-IFN solutions with a final IFN concentration of about 1.3 mg/mL and a $Zn^{+2}$:IFN molar ratio of 2:1, 4:1 or 10:1, respectively. The pH of the $Zn^{+2}$-IFN solution was then adjusted to 7.1 by adding 1% acetic acid. A cloudy suspended precipitate, comprising $Zn^{+2}$-stabilized IFN, formed in each solution.

The suspension of $Zn^{+2}$-stabilized IFN was then micronized using an ultrasonic nozzle (Sonics and Materials, Danbury, CT) and sprayed into a polypropylene tub (17 cm diameter and 8 cm deep) containing liquid nitrogen to form frozen particles. The polypropylene tub was then placed into a −80° C. freezer until the liquid nitrogen evaporated. The frozen particles, which contained $Zn^{+2}$-stabilized IFN, were then lyophilized to form $Zn^{+2}$-stabilized IFN particles.

EXAMPLE 2

Preparation of PLGA Microspheres Containing a 2:1 $Zn^{+2}$:IFN Molar Ratio

PLGA (0.42 g) with an intrinsic viscosity of 0.15 dL/g, obtained from Birmingham Polymers, Birmingham, AL, was dissolved in 4.2 mL of methylene chloride to form a polymer solution. To this polymer solution was added 80 mg of lyophilized $Zn^{+2}$-stabilized IFN particles, containing 2 moles of zinc ions per mole of IFN and about 19 mg of sodium bicarbonate.

The polymer solution and $Zn^{+2}$-stabilized IFN particles were then sonicated using an ultrasonic probe (Virtis, Co., Gardiner, N.Y.) to form a suspension of $Zn^{+2}$-stabilized IFN particles in the polymer solution. The size of the sonicated, $Zn^{+2}$-stabilized IFN particles was between 2–6 microns. The IFN suspension was then placed in a 10 mL gas-tight syringe.

A 168 mL volume of 100% ethanol was added to the round polypropylene tub. This solution was frozen by surrounding the tub with liquid nitrogen. The frozen ethanol was then covered with 500 mL of liquid nitrogen. The IFN suspension was then pumped from the syringe by a syringe pump (Orion Sage Pump Model 355, Orion Research Inc., Boston, Mass.), at a rate of 1.7 mL/min, into an ultrasonic nozzle (Model CV16, Sonics and Materials, Danbury, Conn.) that was placed above the container containing the frozen ethanol covered with liquid nitrogen. The nozzle atomized the IFN suspension into droplets which froze upon contact with the liquid nitrogen and formed microspheres which sank to the surface of the frozen ethanol.

The container was placed into a −80° C. freezer, thereby evaporating the liquid nitrogen and allowing the ethanol to melt. As the ethanol thawed, the microspheres sank into it. When the temperature was lowered to −95.1° C., the methylene chloride was extracted from the microspheres. After 24 hours, an additional 168 mL of 100% ethanol, which was prechilled to −80° C., was added to the container. Three days after the microspheres were prepared, the ethanol/microsphere slurry was filtered using a 0.65 micron Durapore™ membrane (Millipore, Bedford, Mass.). The filtered microspheres were then vacuum dried in a lyophilizer.

EXAMPLE 3

Preparation of PLGA Microspheres Containing a 4:1 $Zn^{+2}$:IFN Molar Ratio

PLGA microspheres were prepared according to the method described in Example 2, with the exception that the 80 mg of $Zn^{+2}$-stabilized IFN particles, which were synthesized as described in Example 1 and then added to the polymer solution, contained 4 moles of $Zn^{+2}$ per mole of IFN and 18 mg of sodium bicarbonate.

EXAMPLE 4

Preparation of PLGA Microspheres Containing a 10:1 $Zn^{+2}$:IFN Molar Ratio

PLGA microspheres were prepared according to the method described in Example 2, with the exception 0.504 g of PLGA was dissolved in 5.04 mL of methylene chloride to form a polymer solution. To this polymer solution was added 96 mg of $Zn^{+2}$-stabilized IFN particles containing 10 moles of zinc ions per mole of IFN, which were synthesized as described in Example 1, and 18 mg of sodium bicarbonate.

Additionally, the IFN suspension was sprayed into a container containing 202 mL of 100% ethanol, covered with liquid nitrogen.

After 24 hours, an additional 202 mL of 100% ethanol, which was prechilled to −80° C., was added to the container.

EXAMPLE 5

Preparation of PLGA Microspheres Containing Magnesium Carbonate And a 2:1 $Zn^{+2}$:IFN Molar Ratio PLGA microspheres were prepared according to the method described in Example 2, with the exception that 40 mg of $Zn^{+2}$-stabilized IFN particles, containing 2 moles of zinc ions per mole of IFN, synthesized as described in Example 1, and 9.5 mg of sodium bicarbonate, were added to the polymer solution. In addition, 40 mg of magnesium carbonate, obtained from Spectrum Chemical Manufacturing Corp., (Gardena, Calif.), and sieved through a 38 micron (#400) sieve, was also added to the polymer solution. After sonicating the polymer solution, the size of the sonicated, $Zn^{+2}$-stabilized IFN particles was between 3–15 microns.

EXAMPLE 6

Preparation of PLGA Microspheres Containing Zinc Carbonate and a 2:1 $Zn^{+2}$:IFN Molar Ratio PLGA microspheres were prepared according to the method described in Example 2, with the exception that 0.436 g of PLGA was dissolved in 4.36 mL of methylene chloride to form a polymer solution. To this solution was added 14 mg of $Zn^{+2}$-stabilized IFN particles containing 0.2 mg zinc acetate dihydrate and 3.3 mg of sodium bicarbonate. Additionally, 50 mg of zinc carbonate was seived through a 38 μM sieve and was then added to the polymer solution.

Furthermore, the IFN suspension was sprayed into a container.

After 24 hours, an additional 174 mL of 100% ethanol, which was prechilled to −80° C., was added to the container.

EXAMPLE 7

Comparison of IFN Encapsulated with Non-Metal Cation Stabilizers to $Zn^{+2}$-Stabilized IFN Dextran 70 (Spectrum Chemical Manufacturing Co., Gardena, Calif.) was added to a solution of IFN α-2,b in 10 mM sodium phosphate buffer at a weight ratio of 1:1 (Dextran:IFN). The solution was micronized through an ultrasonic nozzel as described in Example 1 and the frozen particles were then lyophilized. The IFN dextran particles were subsequently microencapsulated in PLGA as described in Example 2 to form IFN-Dextran microspheres. $Zn^{+2}$-stablilized IFN particles (2:1 $Zn^{+2}$: IFN ratio) were also microencapsulated as described in Example 2 to form $Zn^{+2}$-stabilized IFN microspheres.

In vitro dissolution was conducted on the two microsphere formulations by incubating 20 mg of each type of microsphere in buffer at 37° C. IFN release from the microspheres was monitored by BioRad protein assay (BioRad Inc. Richmond, Calif.).

IFN release from the IFN/Dextran microspheres was linear for the first 10 days with an average release rate of 6.4%/day. The release continued at a rate of 0.4%/day from day 10 to day 14 with a total cumulative release of 66% by day 14. No further release of protein from the microspheres was detected. The microspheres were dried down at day 28. The IFN/Dextran remaining was extracted from the microspheres and the protein was characterized by testing its solubility in water and monomer content by sodium dodecyl sulfate (SDS) polyacrylamide gel electrophoresis (PAGE). Only 18% of the protein remaining inside the microspheres was water soluble. The insoluble protein was solubilized using SDS and run on a gel. The insoluble material contained 19% covalent aggregates and 81% non-covalent aggregates.

In contrast the microspheres with the $Zn^{+2}$-stabilized IFN showed linear release for at least 28 days at a rate of 2.7%/day. The analyses indicate the formulation of IFN with zinc is more stable resulting in a longer period of continuous release of protein from the microspheres.

EXAMPLE 8

In Vivo Release of IFN α-2,b From Polymeric Microspheres

Microspheres, prepared as described in Examples 2–6 were tested in rats for release of IFN α-2,b. Normal rats were obtained from Taconics, Inc. (Germantown, N.Y.). The animals were fed with a standard diet and allowed free access to water. Three to four rats were injected subcutaneously in the interscapular region with a dose of 0.6–2.0 mg IFN/kg rat on day 0 for each of the IFN microspheres of Examples 2–6. Blood samples were taken from the tail vein of each rat at 1, 2, 4, 8, 10 (optionally), 24, 36 and 48 hours after injection. Additional blood samples were then taken approximately once a day for the following 4–5 days. The IFN-α concentration in the rat serum samples was determined using an IFN-α immunoradiometric assay, (Celltech, Slough, U.K), hereinafter "IRMA". The IRMA assay has a limit of quantitation of 9 IU/ml. The IFN-α serum level for control rats, which did not receive the microspheres of Example 1 were found to be less than 9 IU/mL.

Figure 2:
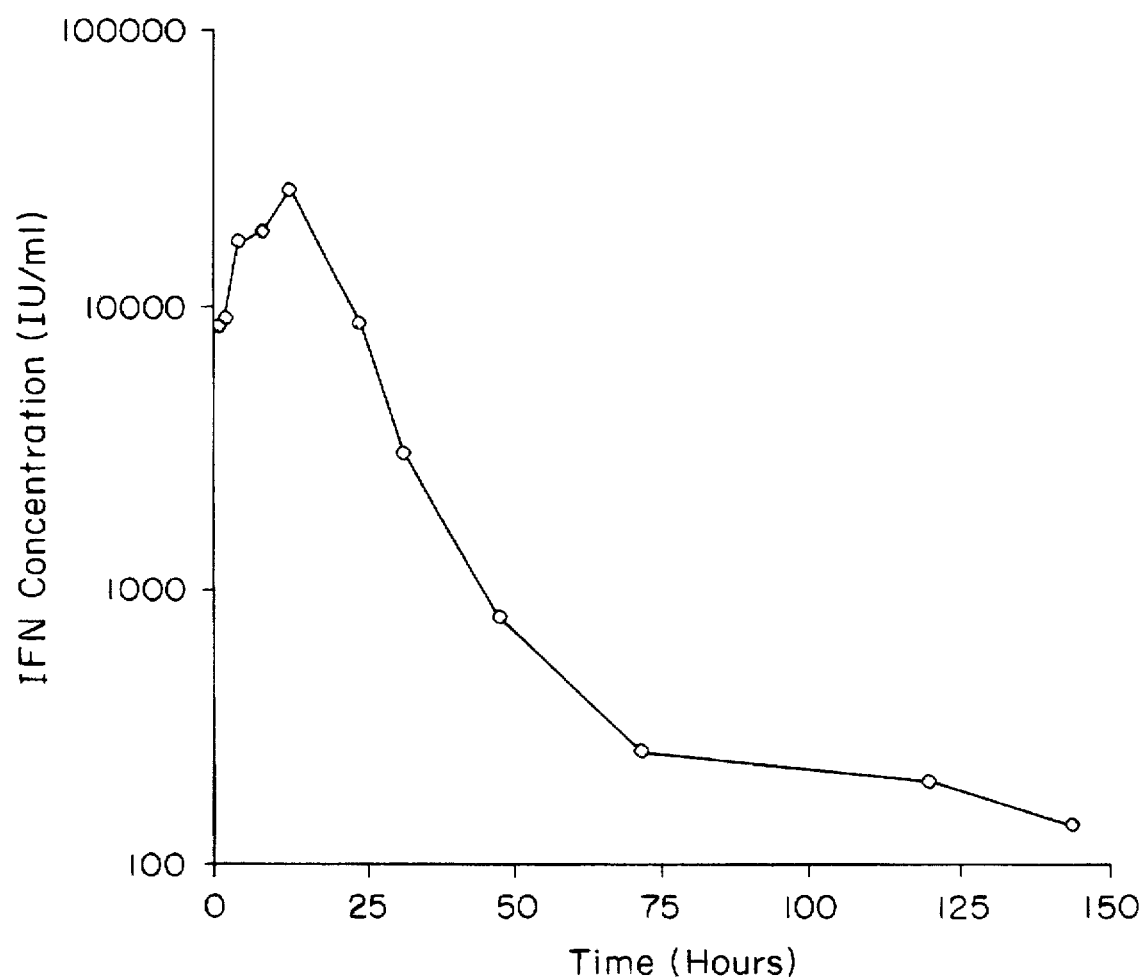
FIG. 2 is a plot of the serum concentration (IU/mL) of Interferon-α,2b in rats which were subcutaneously administered Interferon-α,2b controlled release microspheres of Example 3, versus time over a 6 day interval.
Figure 3:
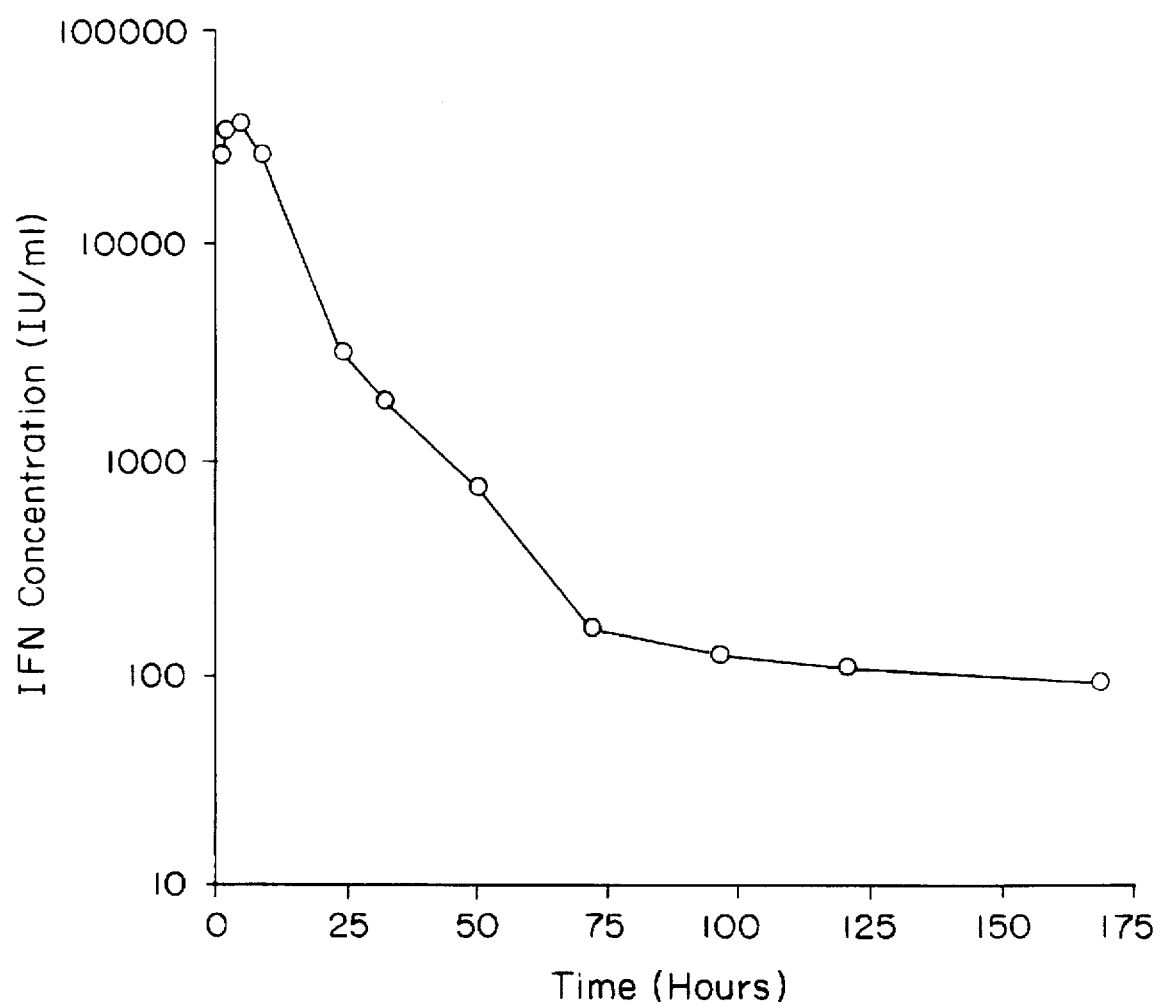
FIG. 3 is a plot of the serum concentration (IU/mL) of Interferon-α,2b in rats which were subcutaneously administered interferon-α,2b controlled release microspheres of Example 4, versus time over a 7 day interval.
Figure 4:
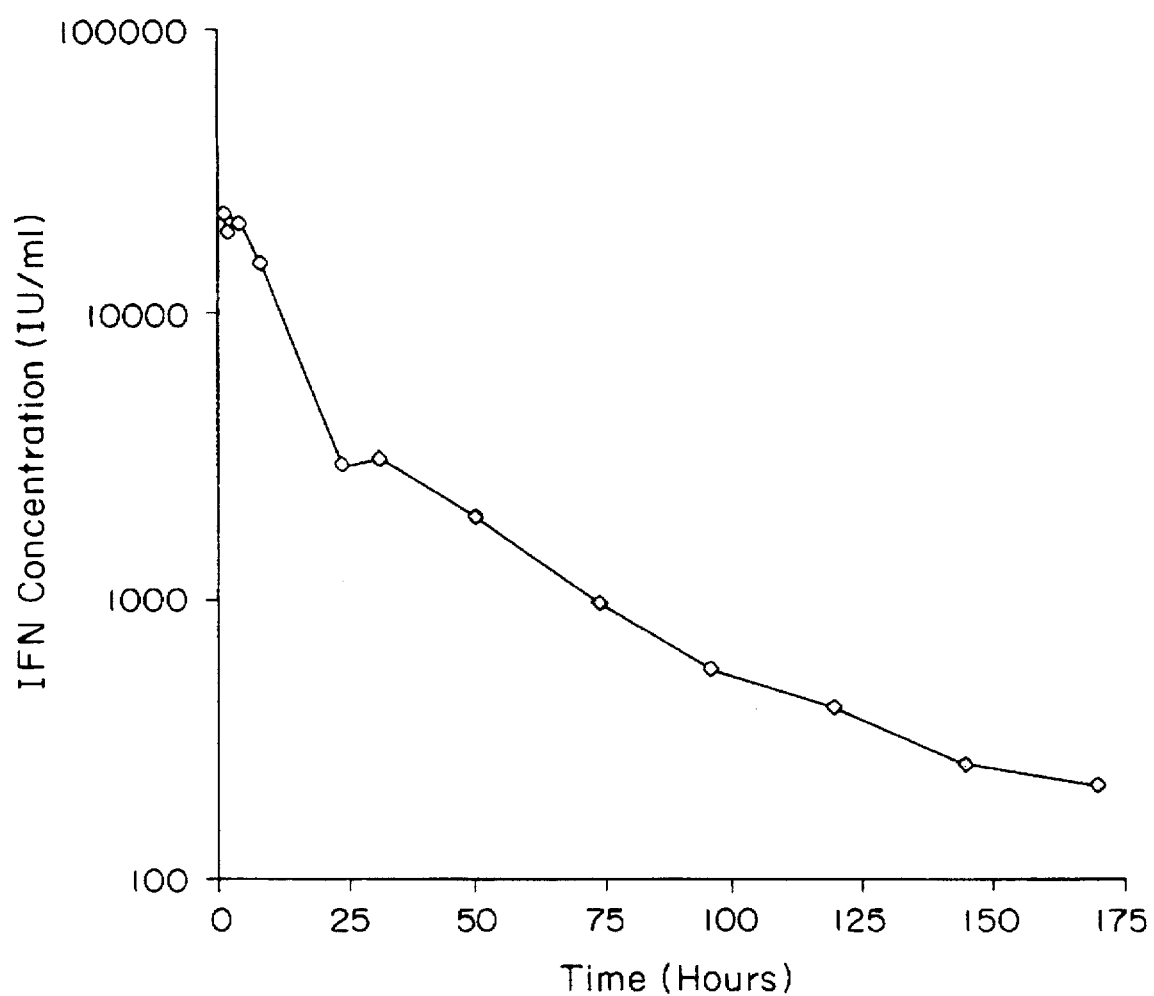
FIG. 4 is a plot of the serum concentration (IU/mL) of Interferon-α,2b in rats which were subcutaneously administered Interferon-α,2b controlled release microspheres of Example 5, versus time over a 7 day interval.
Figure 5:
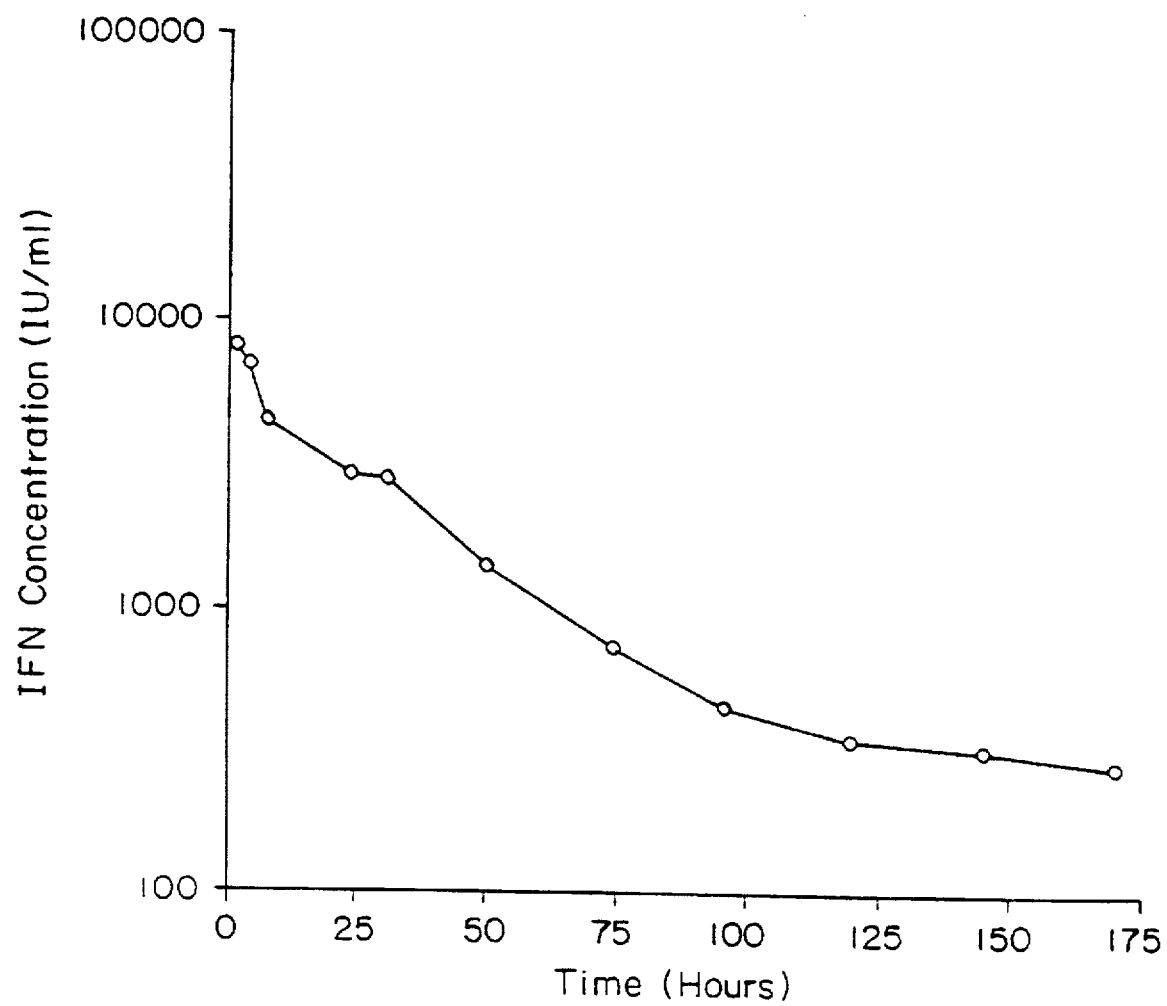
FIG. 5 is a plot of the serum concentration (IU/mL) of Interferon-α,2b in rats which were subcutaneously administered Interferon-α,2b controlled release microspheres of Example 6, versus time over a 7 day interval.

The results of the IRMA assays conducted on the rats receiving the microspheres of Examples 2–6 are shown in FIGS. 1–5. FIGS. 1–5 show that the injectable microsphere formulations of Examples 2–6, respectively, provided a sustained release of immunologically active IFN-α.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A composition for the controlled release of interferon from a polymeric matrix, comprising:
   a) a biocompatible polymer; and
   b) particles of metal cation-complexed interferon, wherein said particles are dispersed within the biocompatible polymer and are in the substantial absence of protamine.

2. A controlled release composition of claim 1 wherein the metal cation-complexed interferon contains at least one type of biocompatible multivalent cation, wherein said cation is not significantly oxidizing to interferon.

3. A controlled release composition of claim 2 wherein said multivalent cation is selected from the group consisting of $Zn^{+2}$, $Ca^{+2}$, $Cu^{+2}$, $Mg^{+2}$ and any combination thereof.

4. A controlled release composition of claim 2 wherein the biocompatible polymer is biodegradable.

5. A controlled release composition of claim 4 wherein the biodegradable polymer is selected from the group consisting of poly(lactides), poly(glycolides), poly(lactide-co-glycolides), polycaprolactone, polycarbonates, polyesteramides, polyanhydrides, poly(amino acids), polyorthoesters, polyacetals, polycyanoacrylates, biodegradable polyurethanes, blends and copolymers thereof.

6. A controlled release composition of claim 5 wherein said polymer comprises poly(lactide-co-glycolide).

7. A controlled release composition of claim 2 wherein the biocompatible polymer is non-biodegradable.

8. A controlled release composition of claim 7, further comprising a pore forming agent which is dispersed within the non-biodegradable polymer.

9. A controlled release composition of claim 8 wherein the non-biodegradable polymer is selected from the group consisting of non-biodegradable polyurethanes, polyacrylates, poly(ethylene-vinyl acetates), poly(acyl-substituted cellulose acetates), polysaccharides, polystyrenes, polyvinyl chloride, polyvinyl fluoride, poly(vinyl imidazole), chlorosulphonated polyolefins, polyethylene oxides, blends and copolymers thereof.

10. A controlled release composition of claim 4 further comprising a second metal cation component, wherein the second metal cation component is not complexed to said interferon, and wherein the second metal cation component is dispersed within the biocompatible polymer to modulate the release of interferon from the polymeric matrix.

11. A controlled release composition of claim 10 wherein the second metal cation component inorganic salt is selected from the group consisting of $Mg(OH)_2$, $MgCO_3$, $CaCO_3$, $ZnCO_3$, $Mg(OAc)_2$, $Zn(OAc)_2$, $ZnSO_4$, $MgCl_2$, $ZnCl_2$, $MgSO_4$, zinc citrate and magnesium citrate.

12. A method for forming a composition for the controlled release of interferon, comprising the steps of:
   a) dissolving a diocompatible polymer in a polymer solvent to form a polymer solution;
   b) dispersing metal cation-complexed interferon particles which are in the substantial absence of protamine, in the polymer solution; and
   c) solidifying the polymer to form a polymeric matrix containing a dispresion of said interferon particles.

13. A method of claim 12 wherein the metal cation of the metal cation-complexed interferon contains at least one type of biocompatible multivalent cation, which is not significantly oxidizing to interferon.

14. A method of claim 13 wherein the multivalent cation is selected from the group consisting of $Zn^{+2}$, $Ca^{+2}$, $Mg^{+2}$, $Cu^{+2}$ and a combination thereof.

15. A method of claim 14 wherein the biocompatible polymer is biodegradable.

16. A method of claim 15 wherein the biodegradable polymer is selected from the group consisting of poly (lactides), poly(glycolides), poly(lactide-co-glycolides), polycaprolactone, polycarbonates, polyesteramides, polyanhydrides, poly(amino acids), polyorthoesters, polyacetals, polycyanoacrylates, biodegradable polyurethanes, blends and copolymers thereof.

17. A method of claim 16 wherein the biodegradable polymer comprises poly(lactide-co-glycolide).

18. A method of claim 13 wherein the biocompatible polymer is non-biodegradable.

19. A method of claim 18, further comprising the step of dispersing a pore forming agent within the polymer solution.

20. A method of claim 19 wherein the non-biodegradable polymer is selected from the group consisting of nonbiodegradable polyurethanes, polyacrylates, poly(ethylene-vinyl acetates), poly(acyl-substituted cellulose acetates), polysaccharides, polystyrenes, polyvinyl chloride, polyvinyl fluoride, poly(vinyl imidazole), chlorosulphonated polyolefins, polyethylene oxides, blends and copolymers thereof.

21. A method of claim 15 further comprising the step of dispersing a second metal cation component within the polymer solution, wherein the second metal cation component is not contained in said interferon particles.

22. A method of claim 21 wherein the second metal cation component is selected from the group consisting of $